United States Patent [19]
Pavlik

[11] 3,956,293
[45] May 11, 1976

[54] TRI (FLUOROALIPHATIC) α FLUOSULFATO AMINES AND DERIVATIVES THEREOF

[75] Inventor: Frank J. Pavlik, St. Paul, Minn.

[73] Assignee: Minnesota Mining and Manufacturing Company, St. Paul, Minn.

[22] Filed: Mar. 12, 1971

[21] Appl. No.: 123,837

Related U.S. Application Data

[63] Continuation of Ser. No. 703,867, Feb. 8, 1968, abandoned.

[52] U.S. Cl............................ 260/246 B; 260/239 B; 260/247.1 R; 260/293.85; 260/326.82; 260/456 A
[51] Int. Cl.$^2$........................................ C07D 265/32
[58] Field of Search ......... 260/247.1, 239 B, 246 B, 260/293.85, 326.82, 456 A

[56] References Cited
OTHER PUBLICATIONS

Sokol'skii et al., Zhur. Obshchei Khim., 31, 2743–2748, (1961).

*Primary Examiner*—G. Thomas Todd
*Attorney, Agent, or Firm*—Alexander, Sell, Steldt & DeLaHunt

[57] ABSTRACT

Tri(fluoroaliphatic amines) wherein there is at least one fluorine atom on one carbon alpha to the tertiary nitrogen are reacted with $SO_3$ to produce tri(fluoroaliphatic) alpha fluosulfato amines which can be hydrolyzed under controlled conditions to produce oxo or hydroxyl derivatives by removal of the fluosulfato group ($OSO_2F$), which derivatives can also be further hydrolyzed to useful products.

11 Claims, No Drawings

TRI (FLUOROALIPHATIC) ALPHA FLUOSULFATO AMINES AND DERIVATIVES THEREOF

This application is a continuation of application Ser. No. 703,867, filed Feb. 8, 1968, now abandoned.

BACKGROUND OF THE INVENTION

1. Field of the Invention

This invention relates to tertiary amine derivatives; more particularly it relates to fluorinated alpha fluosulfato tertiary amines, to processes for making and using same, and to certain novel products derived therefrom.

2. Description of the Prior Art

Heretofore, the perfluorotertiary amines as a class were thought to have as their characteristic feature extreme inertness. The related N-fluoro amines have been shown to react, but through an initial reaction of the nitrogen-bonded fluorine atom. Thus, pyrolytic decomposition of a perfluoro-tertiary amine takes place only at extremely high temperatures. This extreme stability — thermal, electrical, and chemical — has led to important uses for the perfluorotertiary amines such as heat transfer agents for the electrical components of radar signal transmitters.

Sokolov [Chem. Abstr. 63, 1712b, 8309h, (1965)] has reported a reaction between anhydrous $AlCl_3$ and perfluorotertiary amines to give a mixture of compounds resulting from replacement of fluorine by chlorine as well as low boiling products resulting from C—C and C—N cleavage. However, the reaction is nonspecific and results in extensive decomposition.

SUMMARY

By contrast to the prior art, in this invention it has been found that $SO_3$ reacts in a specific manner with perfluoro-tertiary nitrogen containing compounds to form alpha fluosulfato amines in excellent yields (e.g., yields of 60–80% or more of a single derivative based on the amount of starting material consumed). (The fluosulfato group is represented by the structure

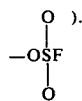

).

An especially useful class of products is the fluorinated carboxylic acids prepared by hydrolysis of certain of the fluosulfato amines of this invention.

The tri(fluoroaliphatic) alpha fluosulfato amines of this invention may be represented by the formula:

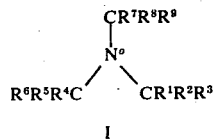

I where $R^1$–$R^9$, inclusive, are fluorine, a fluoroaliphatic radical, or a fluosulfato group (—$OSO_2F$), with the proviso that at least one of the alpha carbon substituents $R^1$–$R^9$ is a fluoroaliphatic group and at least one is a fluosulfato group, with the further proviso that any pair of alpha carbon substituents, one member of the pair of alpha carbon substituents, one member of the pair from one alpha carbon and one from another, e.g., $R_1$–$R_5$, $R_2$–$R_6$, $R_3$–$R_6$, can form an aliphatic heterocyclic ring with the tertiary nitrogen atom ($N^o$) of from about 4 to about 7 members. (The superscript "o" is used to distinguish this nitrogen atom from other N atoms which may be present in one of the alpha fluoroaliphatic substituents.) While it is possible to replace more than one or even all of the alpha fluorine atoms (i.e., fluorine atoms bonded to a carbon which is directly bonded to a tertiary nitrogen atom) with a fluosulfato group, in practice it is usually preferred to run the reaction under such conditions that only a single alpha fluorine is replaced.

Exemplary alpha fluosulfato amines include alpha fluosulfato N-alkyl morpholines of the formula

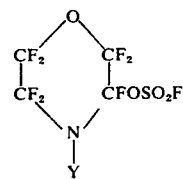

where Y is a perfluoroalkyl radical preferably of less than 20 carbon atoms, e.g. methyl, pentyl, decyl, dodecyl, octadecyl, etc. Tertiary perfluoroalkyl radicals of the formula —$C(Z)_3$ are also preferred, Z being a perfluoroalkyl group, generally of 4 or less carbon atoms, such as $CF_3$, $C_2F_5$—. The bis-morpholine alpha fluosulfato amines of the formula

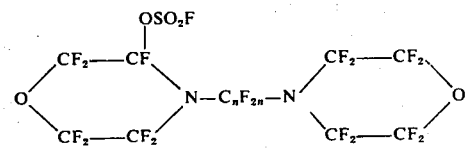

where $n$ is an integer less than about 20 are also exemplary of the compounds of this invention.

The fluoroaliphatic radicals (R) are fluorinated, saturated, aliphatic radicals containing at least one carbon atom in the skeletal chain. Such skeletal chains may be straight, branched, or cyclic, and may be interrupted by trivalent nitrogen or divalent oxygen or sulfur, preferably no more than one such interruption for every two skeletal carbon atoms. Compounds of formula (I) having fluoroaliphatic radicals of less than 20 carbon atoms in the skeletal chain are preferred due to the difficulty of preparation of longer chained radicals. It is preferred to have only carbon and fluorine present as substituents to satisfy nonskeletal valences although an occasional group relatively inert to $SO_3$ such as a hydrogen atom, $SO_2F$, COF, $SO_3H$, $CO_2H$, or $NO_2$ radical or a non-fluorine halogen atom may be present as a substituent on the fluoroaliphatic skeletal chain providing not more than one such non-fluorine non-carbon substituent is present in such radical for every two carbon atoms on the average. Two fluoroaliphatic groups, each on a different alpha carbon may be linked as above stated to form a 4–7 member N-heterocyclic ring, e.g.,

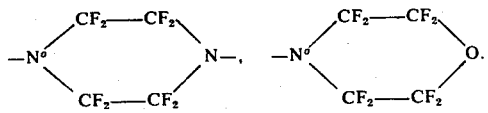

In another aspect, this invention relates to the process of making compounds of Formula I which comprises reacting $SO_3$ with a tri(fluoroaliphatic) amine of the formula

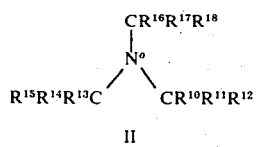

II where $R^{10}$–$R^{18}$ are either fluorine or fluoroaliphatic radicals as defined above with the proviso that at least one is fluorine and at least one is a fluoroaliphatic group. The tri(perfluoroaliphatic) amines are compounds in which the nitrogen atom ($N^o$) is bonded only to carbon atoms, the carbon atoms adjacent to the nitrogen (alpha carbon atoms) being in turn bonded only to fluorine or saturated fluoroaliphatic radicals with the minor exceptions as described above. Typical compounds and their preparation are disclosed in Kauck and Simons, U.S. Pat. Nos. 2,616,927 and 2,631,151.

The minimum molar quantity of $SO_3$ employed is determined by the desired number of alpha fluosulfato groups, e.g., if one fluosulfato group is desired, at least one mole of $SO_3$ per mole of amine is employed, etc. The sulfur trioxide may be free $SO_3$ or may be combined as for example in fuming sulfuric acid, $H_2S_2O_7$; $HSO_3F$, and the like. A particularly useful form of $SO_3$ is "Sulfan B" (Allied Chemical Co.), a liquid stabilized against spontaneous conversion to the thermo-dynamically preferred solid form. It is preferred to keep the reaction mixture substantially anhydrous and free of contaminants or solvents which would react with $SO_3$. Moisture lowers the yield of alpha fluosulfato product although minor amounts of moisture (e.g., as sulfuric acid) can be present when the $SO_3$ is contacted with the tertiary amine. Thus, it is preferred to conduct a reaction under anhydrous conditions, and in general there should not be more than 1% by weight water present in the total reaction mixture.

The reactor construction is not critical. Glass, as well as corrosion resistant materials such as stainless steel, nickel, monel and the like are suitable. Reaction temperatures can vary widely, but in general temperatures in the range of from about 55° to 200°C. are desirable, and temperatures in the range of from about 60° to 150°C. are preferred.

Particularly when a batchwise reaction between a tertiary amine and $SO_3$ is being undertaken, it is convenient and preferred to maintain the reactants below about 30°C. until admixture of reactants is accomplished in order to maximize product yields and improve ease of operation.

Reaction pressures in excess of atmospheric are preferable in order to maintain reactants in intimate contact and thereby promote reaction. Autogenous pressures are especially desirable.

Reaction times vary but in general are in the range of from about 3 to 24 hours. Completion of a reaction is indicated by establishment of a constant pressure at constant temperature.

In still another aspect, this invention relates to compounds of the formula

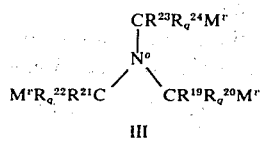

III where $R^{19}$–$R^{24}$, inclusive, are fluorine or a fluoroaliphatic group, M is fluorine, a fluoroaliphatic group, a hydroxyl group, or an oxo group (=O), $v$ is the valence of M, $q$ denotes the number of $R^{20}$, $R^{22}$, and $R^{24}$ groups, $q$ being 1 when $v=1$ and O when $v=2$ (i.e., M is =O), with the proviso that there is at least one M which is the monovalent radical OH or the divalent radical =O, and at least one R group which is fluoroaliphatic, and with the further proviso that any pair of alpha carbon fluoroaliphatic substituents, one member from one alpha carbon and one from another, can form a heterocyclic ring with the nitrogen atom ($N^o$) of from 4 to about 7 members.

DESCRIPTION OF THE PREFERRED EMBODIMENTS

The compounds of formula III may be prepared by controlled hydrolysis of the alpha fluosulfato compounds (I). For controlled hydrolysis, a stoichiometric amount of water is preferred, although an excess may be employed. Temperature is not critical. Below about 0° C., the rate of reaction is impractically slow, while above about 350°C. decomposition of the product amide occurs. A reasonable rate is usually obtained between about 50° and 75° C. The reaction proceeds in the presence of water without a catalyst although an acid catalyst such as $H_2SO_4$ is preferred. The preferred procedure is to add the water as concentrated (e.g., 94–96% by weight) sulfuric acid, which contains 4–6% water in a form which readily hydrolyzes the fluosulfato group but reacts considerably more slowly with the

group.

A weak base such as an organic amine, particularly a tertiary amine, can be used; strong bases such as sodium hydroxide can cause further hydrolysis of the product amide, and therefore are usually avoided. The amide can be isolated from the fluorocarbon phase by distillation. Distillation at reduced pressure is preferred for higher boiling compounds, e.g., those with 10 or more carbon atoms. The resulting amides are stable compounds which are usually liquids or low-melting solids.

Further hydrolysis of the amide or alcohol (III) will lead to a variety of products depending on the structure of the amide or alcohol. Hydrolysis may take place directly through the usual "displacement" reaction by a water molecule or a hydrated H$^+$ or OH$^-$ ion or by means of an initial loss of a small molecule, such as HOH or HF, to form a

structure which then adds the elements of HOH. The adduct may be stable or may continue with similar reaction sequences to a composition which is stable to further hydrolysis.

Although water is used in the discussion herein, similar small polar solvent molecules containing active hydrogen such as alcohols, ammonia, amines, amides and the like, enter into similar "solvolytic" reactions.

With regard to the intermediate and ultimate products formed by initial reaction of $SO_3$ with tri(fluoroaliphatic) amines followed by hydrolysis, six general situations can occur, as illustrated below. In these examples "R" indicates a monovalent fluoroaliphatic radical and F a fluorine radical.

A. $(R_3C)_3N + SO_3 \rightarrow$ No reaction. Since no fluorine radicals are attached to the $\alpha$ carbon atoms, $SO_3$ does not attack the molecule under the conditions considered here, where temperatures are generally below about 200°C.

B. In this situation, at least one $\alpha$ carbon atom has only one fluorine atom attached thereto.

$(CR_3)_2NCR_2F\ SO_3 \rightarrow (CR_3)_2NCR_2OSO_2F\ H_2O$
$\rightarrow (CR_3)_2NCR_2OH$ The resulting $\alpha$ hydroxy compound is stable to further reaction since the atom bearing the —OH radical is free of fluorine and the adjacent skeletal atoms are free of hydrogen. Hence, neither water nor HF can readily be released to initiate a site for further reaction.

If either or both of the other two $\alpha$ carbon atoms bear a single fluorine atom, the above sulfation reaction and hydrolysis can be repeated, resulting in a stable diol or triol. It should be noted that an alcohol retaining unreacted fluorine atoms on non-hydroxyl-bearing $\alpha$ carbon atoms is stable to hydrolysis. For example, the structure

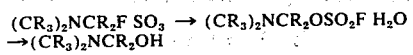

is hydrolytically rather stable, although for example in the presence of acids further hydrolysis is feasible.

C. The structure includes one $\alpha$ carbon atom bearing two fluorine atoms, the other two being fluorine-free.

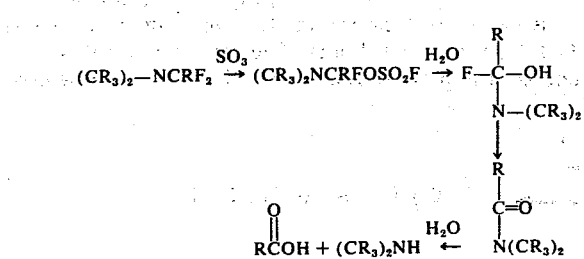

Since there are no fluorine atoms on the remaining $\alpha$ carbon atoms, the secondary amine is stable. Exemplary of compounds having the formula $(CR_3)_2NH$ is $[(CF_3)_3C]_2NH$.

D. The structure includes one $\alpha$ carbon bearing two fluorine atoms, one other $\alpha$ carbon atom bearing only one fluorine atom, and the third bearing no fluorine atoms.

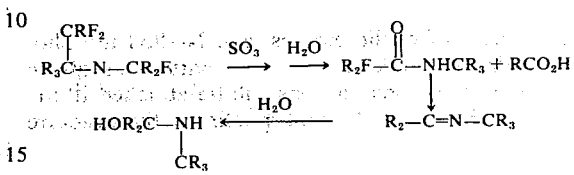

Lacking further reaction sites, the hydroxy amine, or amino alcohol, will not further hydrolyze under ordinary conditions. The last reaction is probably reversible, the amino alcohol losing water to form an imine in the presence of heat, dehydrating reagents, etc. Exemplary of compounds having the formula $HOR_2C$—N—H—$CR_3$ is $HO(CF_3)_2CNHC(CF_3)_3$.

E. If two of the alpha carbon atoms hold two or more fluorine atoms and the third has no fluorine, the following reaction series will be possible.

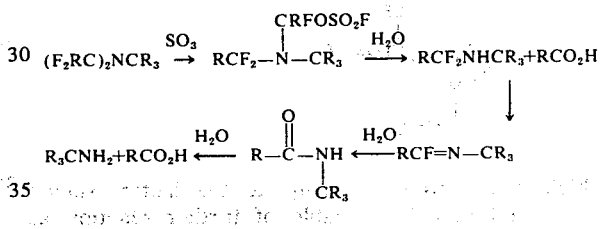

In this case, if the R on the $CF_2$ group were F, $CO_2$ and HF would result rather than $RCO_2H$. Exemplary of compounds having the formula $R_3CNH_2$ is $(C_2F_5)_3CNH_2$.

F. If two carbon atoms have two (or more) fluorine atoms, and the third one fluorine atom, the following reaction sequence may result.

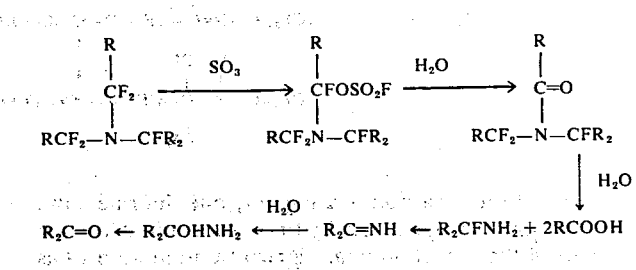

The intermediate amino alcohol will be stable in non-aqueous systems and in the absence of acidic materials, including materials which complex with or solvate ammonia. In this case the C—N linkage will readily break with less than two fluorine atoms being present on the $\alpha$ carbon. Exemplary of compounds having the formula $R_2COHNH_2$ is $(CF_3)_2COHNH_2$.

G. All three $\alpha$ carbon atoms are

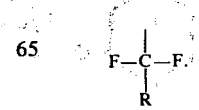

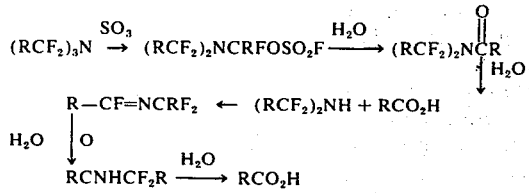

```
R—CF=NCRF₂  ←  (RCF₂)₂NH + RCO₂H
H₂O  | O
     ↓        H₂O
     RCNHCF₂R ——→ RCO₂H
```

In the case of cyclic amines, e.g. N-alkyl morpholines, hydrolysis follows the same pattern as above except that two alpha carbons will be attached in the same chain. For example, a morpholine of the structure

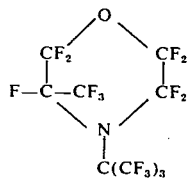

may react to form a fluosulfato derivative

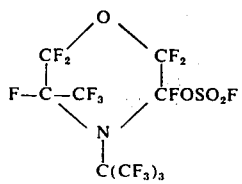

which will hydrolyze initially to the lactam shown below and then be capable of further reaction as shown:

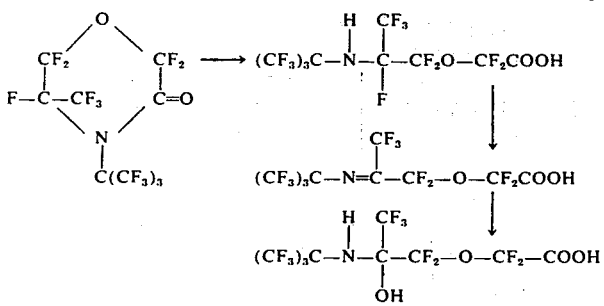

Note that the α carbon bearing only one fluorine atom underwent change to an hydroxy substituted carbon whereas the α carbon bearing two fluorine atoms has become part of a carboxyl group in the same fashion as the analogous compound illustrated in part D above. Similarly, a cyclic compound such as perfluoro(N-ethyl morpholine) would, upon a similar sequence of reactions, hydrolyze to form a monobasic and dibasic acid by analogy to part E above:

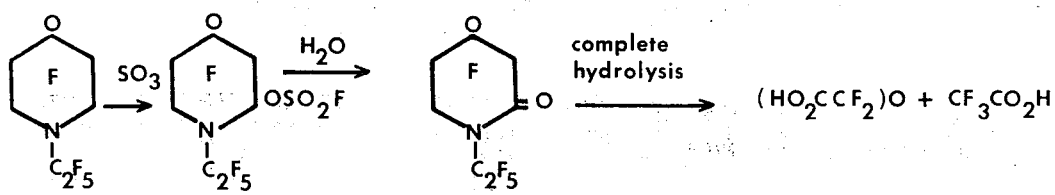

The following examples will further serve to illustrate the invention. All parts and percentages expressed herein are by weight unless otherwise stated.

EXAMPLE I

Preparation of Perfluoro-[N-methyl-3-fluosulfato-morpholine]

To a 300 ml. autoclave is charged 90 g. (0.3 moles) of perfluoro-N-methylmorpholine (b.p. 52°C.) and 24 ml. (0.6 moles) of sulfur trioxide ($SO_3$) and the contents heated at 90°C. with rocking for 16 hours. After cooling, the autoclave is opened and the contents distilled to yield 71.5 g. of liquid, b.p. 105°–108°C./740 mm.

The results of analysis for hydrolyzable fluoride are:
Calc'd. for $C_5F_{11}NO_4S$ - 5% by weight.
Found - 5% by weight.
Other analysis shown:

a. M.W. (found) - 379. M.W. (Calc'd) for $C_5F_{11}NO_4S$ - 379.

b. Mass spectroscopy reveals $CSO_3$ fragment.

c. IR and NMR support the 3-fluosulfato structure.

EXAMPLE II

Complete Hydrolysis of Perfluoro [N-methyl-3-fluosulfato-morpholine]

Perfluoro [N-methyl-3-fluosulfato-morpholine] is hydrolyzed with a 25% aqueous KOH solution at 70° C. for 3 hours. The reaction mixture is then evaporated to dryness at 90°–100° C. The remaining solids are extracted with anhydrous methanol to yield 91 g. of the potassium salt of oxydifluoroacetic acid. To a reaction vessel containing 77 g. of this salt is added 126 g. of dimethylsulfate. The reaction mixture is heated to 70° C. with stirring overnight. Methanol (100 ml.) is then added and the reaction mixture refluxed for 3 hours. Distillation yields dimethyl oxydifluoroacetate O(CF₂COOCH₃)₂ (b.p. 50° C./2 mm. Hg.), identified by comparison of its infrared spectrum with that of a known sample.

EXAMPLE III

Preparation of Perfluoro [-N-(diethylaminopropyl)-3-fluosulfato-morpholine]

Perfluoro-N-(diethylaminopropyl) morpholine, 325 g., is heated with 50 ml. of stabilized sulfur trioxide at 140° C. for sixteen hours. The reaction vessel is then cooled, the product removed and stripped of low boiling materials (b.p. < 110° C.). The residual product weighs 361 g.

To 72 g. of this product is added 150 ml. of water and 40 g. of $KHCO_3$, and the reaction mixture stirred at 70°–78° C. overnight (16 hrs.). Perfluoro-N-methyl-morpholine (100 ml.) is then added with stirring. The lower phase is separated and cooled to yield 6 g. of white solid, m.p. 88°–90°C. The infrared spectrum shows an —NH absorption at $2.95\mu$ and a strong carbonyl absorption at $5.8\mu$. Elemental analysis: Found; N, 7.4; F, 66.0 calculated for $(C_2F_5)_2 NCF_2CF_2CONH_2$: N, 7.07; F, 67.2. Saponification of 2.0 g. of this material with aqueous KOH, then acidification, yielded 1.8 g. of acid which assayed 94% as $(C_2F_5)_2NCF_2CF_2COOH$ by titration with base.

EXAMPLE IV Preparation and Hydrolysis of Perfluoro[N,N'decamethylene-bis-3-fluosulfato-morpholine]

A rocking autoclave is charged with 25 g. of crude, solid perfluoro-N,N'-decamethylene bis-morpholine and 30 ml. of $SO_3$. Agitation for 16 hours at 140° C. yields the bis-3-fluosulfato derivative. To the reaction mixture which is cooled in a cold water bath is added dropwise 32 g. KOH in 100 ml. $H_2O$. The reaction temperature rises to 55° C. Additional KOH is added until the pH is about 12. The mixture is stirred overnight, then evaporated to dryness on a steam bath and extracted first with perfluoro-N-isopropylmorpholine (25 ml.) two times to remove unreacted N,N'-decamethylene-bis-morpholine (2.3 g. is recovered). The solids are then extracted with 100 ml. portions of anhydrous methanol five times, 25.8 g. of salts being recovered. Infrared spectroscopy shows the soluble salts to be perfluorocarboxylic salts with a strong absorption at $6.1\mu$ for the carbonyl and 8.1 to $8.5\mu$ for carbon-fluorine bonds. Twenty-four grams of the salts is treated with 100 ml. anhydrous methanol and 50 ml. conc. $H_2SO_4$ at 50° C. for 16 hours. The reaction contents are further treated with 24 g. of dimethyl sulfate for two hours to complete the reaction. Ethylene chloride, 100 ml., is then added followed by 100 ml. of water to separate the esters from methanol, sulfuric acid and unreacted dimethyl sulfate. The aqueous upper layer is further extracted with 100 ml. ethylene chloride. The extracts are combined and dried with sodium sulfate, then distilled at atmospheric pressure to remove the ethylene chloride and some methanol. Vacuum distillation at 50° C./3mm. Hg gives 2.0 g.; at 66° C./3mm. Hg, 2.8 g., and a third fraction at 66° C./2mm. Hg, 1.4 g. Titration of the latter two fractions with sodium methoxide shows 94% and 101% respectively as $CH_3OOC(CF_2)_8COOCH_3$. Acidification of the sodium salts from the titrations yields from fraction 2 a solid, m.p. 149°–154° C.; from fraction 3, a solid, m.p. 152°–157° C. Fractions 2 and 3 are combined and assayed for dimethyl perfluorosebacate by gas-liquid chromatography; area calculation shows 80% purity, retention time agreeing with that for authentic dimethyl perfluorosebacate.

EXAMPLE V

In Situ Preparation of Perfluoro(N-methyl-3-oxo-morpholine)

To 253 g. (0.85 mol) of perfluoro-(N-methyl-morpholine) in a 300 ml. autoclave is added 72 g. (0.9 mol) of sulfur trioxide. The vessel is sealed, heated and rocked at 120° C. for 8 hrs. The autoclave is then cooled to 25° C., vented to release volatile materials and the residue charged to a 500 cc. flask equipped with magnetic stirrer, dropping funnel, condenser and thermometer. A solution of 195 g. of 96% sulfuric acid and 5 g of $H_2O$ is added dropwise with stirring. The temperature is kept below 50° C. After the sulfuric acid is added the mixture is heated and stirred at reflux (55°–60° C.) for hour hours. Distillation yields a large fraction, 207 g., b.p. 48°–65° C./740 mm., which consists of 45% by weight perfluoro-N-methyl-3-oxo-morpholine (40% conversion) and 15% by weight of higher boiling products believed to include perfluoro-(N-methyl-3,5-dioxo-morpholine). Isolation of the pure amide (b.p. 59°–60° C./740 mm.) can be accomplished by distillation through a 25-plate column.

EXAMPLE VI

Alcoholysis of Perfluoro-(N-methyl-3-oxo-morpholine) to Diethyl Oxydifluoroacetate.

A 1 l. flask is charged with 201 g. of the crude distillate of Example V and 170 ml. of 95% ethyl alcohol is added dropwise with stirring. The reaction is exothermic and must be moderated with cooling during the alcohol addition. The reaction mixture is stirred overnight at room temperature, then at reflux for 48 hrs. Considerable solids are formed and an additional 50 ml. of absolute ethyl alcohol is added at reflux and heating continued for one hour. The mixture is then cooled, filtered, and the filtrate distilled to give 63.4 g. (67% yield) crude diethyl oxydifluoroacetate ($n_D^{28}$ 1.3605, b.p. 47°–50° C./1mm.) Assay by gas chromatography gives a purity of 87%.

EXAMPLE VII

Polymerization of Perfluoro-(N-methyl-3-oxo-morpholine)

Thirty-four grams of 98% pure perfluoro-N-methyl-3-oxo-morpholine) is irradiated in a quartz reactor with a 450-watt Hanovia lamp for 66 hours. The unreacted and low boiling materials are then distilled to leave a yellow clear liquid, 1 g., which does not boil at 195° C. The reaction is repeated with fresh material for 112 hours. Distillation yields 2.2 g. of high boiling liquid which infrared spectroscopy shows to contain carbonyl fluoride and perfluoro polyamide linkages as well as carbon-bonded fluorine. Gas chromatography shows the presence of dimers, trimers and higher boiling materials.

EXAMPLE VIII

Preparation of Perfluoro-alpha-fluosulfato-triethylamine

To 25 g. (.067 m.) of $(C_2F_5)_3N$ in a glass ampoule is added 7.5 ml. sulfur trioxide. The ampoule is sealed and heated at 85° C. in a water bath with rotation for 16 hours. The ampoule is then cooled, opened, and charged to a distillation flask. Distillation at 61° C./60 mm. Hg. yields 5.3% g. of sulfonated material. Purification by gas chromatography and analysis by fluorine nuclear magnetic resonance spectroscopy shows the following structure:

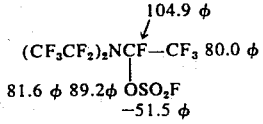

EXAMPLE IX

Reactions of Perfluoro-diethyl-n-propylamine $(C_2F_5)_2NC_3F_7$, 104 g., and $SO_3$, 40 g., are charged to a 300 ml. autoclave and heated at 139° C. for 16 hours. Distillation gives low boiling (< 85° C.) starting material (49 g.) and crude fluosulfato material, 83 g., b.p. 85°–136° C. Saponification of 69 g. of the latter material with excess aqueous KOH at 70° C. overnight is then conducted and unreacted fluorocarbon (33.5 g.) removed by distillation. Evaporation of the residue and extraction of the dried salts with methanol yields 43 g. of the potassium salts of trifluoroacetic and pentafluoropropionic acid. Infrared spectroscopy of these salts show carboxylate, $5.9\mu$ and CF, $8.3\mu$ absorptions. Acidification with concentrated sulfuric acid and distillation therefrom yields 7.7 g. of a mixture of $CF_3COOH$ and $CF_3CF_2COOH$, 28% yield. Infrared spectroscopy confirms the structures. Esterification with n-butanol according to the method of Husted and Ahlbrecht, J. Am. Chem. Soc. 75, 1605, (1953) and comparison with an authentic mixture of butyl trifluoroacetate and butyl pentafluoropropionate by gas chromatography also show these acids to be $CF_3COOH$ and $CF_3CF_2COOH$.

EXAMPLE X

Preparation and Alcoholysis of Perfluoro-N,N'[hexamethylene bis-3-fluosulfato-morpholine]

Perfluoro-(N,N'-hexamethylene-bis-morpholine) (80 g., 0.1 moles) and 57 g. of sulfur trioxide are reacted at 140° C. for 21 hours in a 300 ml. rocking aminco autoclave. The reactor is cooled and vented of gases, then opened, the contents are charged to a distillation pot, and stripped of low boilers. A residue of 87 g. is recovered, 22.3 g. of which is treated with 50 ml. of 95% ethyl alcohol at room temperature for 16 hrs. and then at reflux for one hour with an additional small amount of ethyl alcohol. The reaction mixture is then filtered and the filtrate distilled in vacuo. Two fractions are obtained: (1) 7 g., b.p. 90° C./20 mm., containing 32% diethyl perfluoroadipate; (2) 4.2 g., b.p. 85° C./3mm., containing 16.7% diethyl perfluoroadipate as shown by gas chromatography.

EXAMPLE XI

Preparation of Perfluoro-(N-isopropyl-3-fluosulfatomorpholine)

Perfluoro-N-isopropylmorpholine, 80 g., and sulfur trioxide, 17 g., are heated at 115° C. in a 300 ml. stainless steel pressure vessel for 16 hours. The reaction contents are cooled to room temperature, charged to a glass distillation flask and distilled. Infrared spectroscopy shows the higher boiling fraction (67° C./44 mm. Hg) to have a strong absorption at $6.75\mu$ characteristic of the fluosulfato group.

EXAMPLE XII

Preparation of Perfluoro(-N-ethyl-3-fluosulfato-morpholine)

Perfluoro-N-ethylmorpholine, 70 g., is heated with 17 g. of sulfur trioxide at 85° C. under autogenous pressure for seven hours in a stainless steel pressure vessel. The reaction vessel is then cooled to 25° C. and the contents stirred with 36 g. of 90% sulfuric acid at 25° C. for 90 minutes to remove unreacted sulfur trioxide. Separation of the fluorocarbon phase and distillation gives a fraction boiling at 126°–128° C. Fluorine NMR spectroscopy of this fraction shows the alpha fluosulfato group to be present with characteristic absorption in the infra red at $6.75\mu$.

EXAMPLE XIII

Preparation of Perfluoro(-N-cyclohexyl 2-fluosulfato-piperidine)

To a stainless steel 300 ml. autoclave are charged 256 g. (0.5 m.) of perfluoro-N-cyclohexylpiperidine and 46 ml. of stabilized sulfur trioxide. The autoclave is sealed and the contents heated at 160° C. for 15 hours with rocking, then cooled, removed and distilled. The fraction (35.6 g.) boiling at 168°–180° C. shows a strong fluosulfato absorption at $6.72\mu$.

Other amines from which may be derived exemplary fluosulfato and hydrolysis derivatives are set forth in Table I.

TABLE I

| Amine | Fluosulfato Derivative | Hydrolysis Product |
|---|---|---|
| $CF_3N-(C_8F_{17})_2$ | $FSO_2OCF_2N(C_8F_{17})_2$ | $C_7F_{15}COOH$ |
| $(CF_3)_2N-C_{18}F_{37}$ | $FSO_2OCF_2-N(CF_3)\ C_{18}F_{37}$ | $C_{17}F_{35}COOH$ |
| 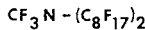 $N-C_8F_{37}$ | 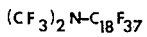 $N-C_8F_{17}$, $OSO_2F$ | $(CF_2COOH)_2 + C_7F_{15}COOH$ |
| 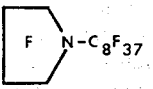 $O\ F\ N-C_{12}F_{25}$ | 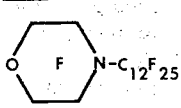 $O\ F\ N-C_{12}H_{25}$, $OSO_2F$ | $O(CF_2COOH)_2 + C_{11}F_{23}COOH$ |
| 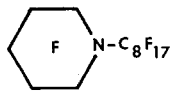 $F\ N-C_8F_{17}$ | $F\ N-C_8F_{17}$, $OSO_2F$ | $CF_2(CF_2COOH)_2 + C_7F_{15}COOH$ |

TABLE I-continued

| Amines | Fluosulfato Derivative | Hydrolysis Product |
|---|---|---|
| 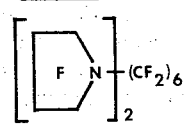 | 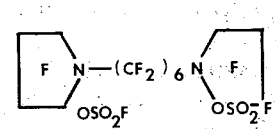 | 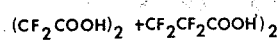 $(CF_2COOH)_2 + CF_2CF_2COOH)_2$ |
| 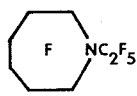 | 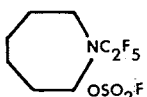 | 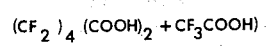 $(CF_2)_4(COOH)_2 + CF_3COOH$ |
| 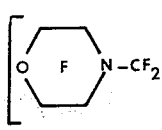 | 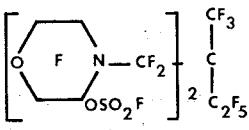 | 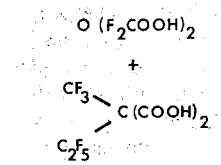 |
| 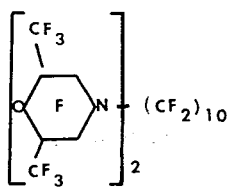 | 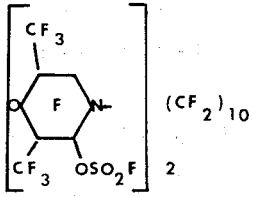 | 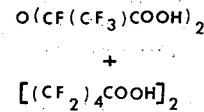 |
| 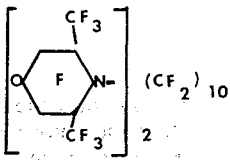 | 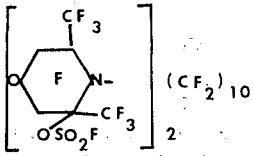 | 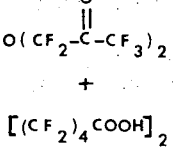 |
| 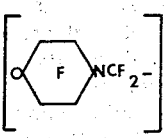 | 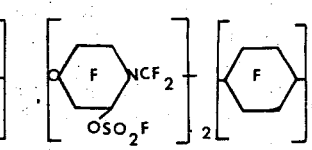 | 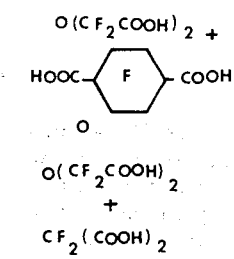 |
| 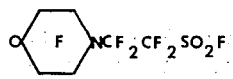 | 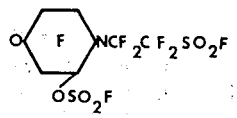 | 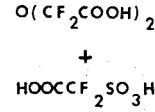 |

The novel fluosulfato compounds of formula I as well as the compounds of formula III above, which may be prepared by selective hydrolysis of the fluosulfato compounds, find their primary utility in conversion to further hydrolysis products as described above. The lower monobasic acids (e.g. those having a fluoroaliphatic radical of 1–3 carbons such as perfluoroacetic acid and perfluoropropionic acid) are well known compounds useful primarily as catalysts and solvents. Trifluoroacetic acid anhydride, prepared by conventional techniques from the corresponding acid, is an esterification catalyst for fluorine-free carboxylic acids. The longer chain perfluorocarboxylic acids, e.g. those having 4 or more skeletal carbons, are useful in preparing oil and water repellent coatings by conversion according to established techniques to the alcohol, then to the acrylate, and finally to polymers and copolymers for textile treatment. Ahlbrecht, U.S. Pat. No. 2,642,416 discloses such monomeric acrylates and homopolymers and copolymers derived therefrom for textile treatment. The perfluoro carboxylic acids can also be converted to Werner complexes such as the chromium complexes disclosed in Reid, U.S. Pat. No. 2,662,835 which are useful in the treatment of paper to impart oil and water repellency.

The dibasic acids formed by hydrolysis of the fluosulfato derivatives of cyclic amines such as the N-substituted piperidines and morpholines, are useful for the preparation of solvent resistant and thermally stable polymers such as polyesters and polyamides. Gaskets and sealants made from such polymers are resistant to hydraulic fluids and lubricants. Polymers prepared from dibasic acids having a skeletal oxygen atom, derivable from perfluoro-N-substituted morpholines, for example, are particularly valuable because of the low temperature flexibility conferred by the skeletal oxygen.

The perfluoro ketones find utility as a co-reactant with epoxides as described in Fawcett et al., U.S. Pat. No. 3,316,216 to prepare polyfluoroketone/1,2-epoxide copolymers useful as coatings for flexible and rigid substrates to impart water insensitivity to said substrates as well as self-supporting films. Perfluoroketoacids are useful as surfactants, the keto group enhancing solubility in portic solvents.

The fluorinated aminoalcohols, including aminoalcohol acids formed on hydrolysis of certain compounds encompassed by formula I, find utility as solvents and plasticizers for polar high polymers, particularly with molecular weights of 50,000 and higher, especially poly(oxymethylene) polymers soluble with difficulty in conventional solvents. To this extent, they are analogous to the perfluoro tertiary alcohols disclosed in Middleton, U.S. Pat. Nos. 3,227,674 and 3,245,944. The fluorinated aminoalcohols of this invention can also be converted by reaction with acrylyl chloride or methacrylyl chloride in the presence of a tertiary amine such as pyridine to form the corresponding acrylate and methacrylate esters and amides which are polymerizable to polymers suitable as oil and water repellent coatings.

The cyclic amides or lactams formed on hydrolysis of cyclic α-fluosulfato amines may be represented by the formula

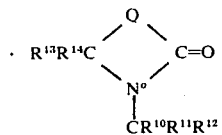

where Q is a divalent fluoroaliphatic radical containing from 1 to about 4 skeletal atoms and preferably with an overall carbon atom content of less than about 20, Q being such that its skeletal chain may contain a trivalent nitrogen or an oxygen atom bonded only to carbon atoms, (e.g.

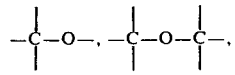

etc.), and $R^{10}$–$R^{14}$ inclusive, are fluorine or fluoroaliphatic radicals as defined above.

Lactams of the above formula may react under free radical generating conditions such as thermal activation, decomposition of free-radical generating chemical compounds, actinic light, and the like to break the carbonyl carbon-nitrogen ($N^o$) bond and polymerize to a linear or cyclic polyamide containing the repeating unit

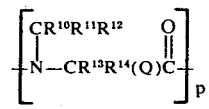

where $p$ is an integer greater than 1. The lower molecular weight polymers, particularly where $p$ is 2 or 3, may be either linear or cyclic. Polymers in which $p$ is higher than 3 tend to be predominantly linear. Liquid polymers are chemically and thermally stable and are useful as lubricant base stocks, coolants, and the like. Solid polymers are useful as chemical resistant, oil and water-repellent coatings. Very high molecular weight polymers where $p$ is on the order of 50 or higher can be cast into self-supporting films, drawn into fibers, in both of which forms they provide chemically and thermally resistant materials. For example, the lactam of Example 7 (perfluoro-[N-methyl-3-oxo-morpholine)] of the formula

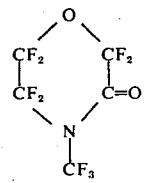

is polymerized by actinic radiation to polymers containing the repeating unit

I claim:
1. The compound represented by the formula:

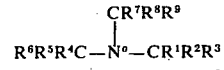

wherein $R^1$ through $R^9$ are alpha-carbon substituents selected from the class consisting of fluorine, fluoroaliphatic having no more than 20 carbon atoms in the skeletal chain, and fluosulfato ($-OSO_2F$), with the proviso that at least one of $R^1$ through $R^9$ is fluoroaliphatic and at least one is fluosulfato, and with the further proviso that any pair of alpha-carbon substituents, one member of the pair from one alpha carbon and one from another, can form a pyrrolidino, piperidino, hexamethyleneimino, or morpholino ring.

2. The compound represented by the formula:

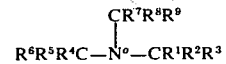

wherein $R^1$ through $R^9$ are alpha-carbon substituents selected from the class consisting of fluorine, fluoroaliphatic having no more than 20 carbon atoms and fluosulfato ($-OSO_2F$), with the proviso that one of $R^1$ through $R^9$ is fluosulfato and with the further proviso that any pair of alpha-carbon substituents, one member of the pair from one alpha carbon and one from another, can form a pyrrolidino, piperidino, hexamethyleneimino, or morpholino ring.

3. The compound represented by the formula:

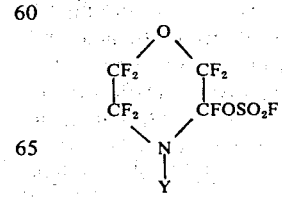

wherein Y is perfluoroalkyl radical having no more than 20 carbon atoms.

4. The compound represented by the formula:

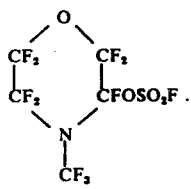

5. The compound represented by the formula:

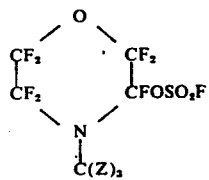

wherein Z is a perfluoroalkyl group having no more than 4 carbon atoms.

6. The compound represented by the formula:

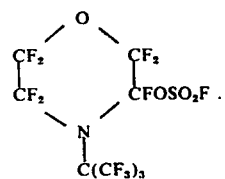

7. The compound represented by the formula:

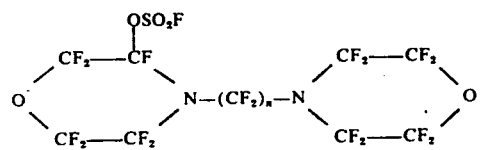

wherein $n$ is an integer less than 20.

8. The compound represented by the formula:

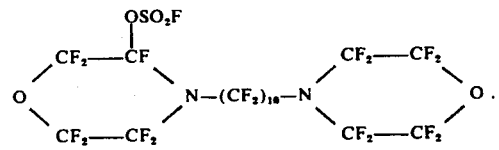

9. The process for preparing tri-(fluoroaliphatic) alpha-fluosulfato amine comprising intimately contacting and reacting $SO_3$, at a temperature in the range of 55° to 200° under autogeneous pressure, with tri-(fluoroaliphatic) amine of the formula:

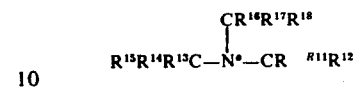

wherein $R^{10}$ through $R^{18}$ are alpha-carbon substituents selected from the class consisting of fluorine and fluoroaliphatic with the proviso that at least one of said $R^{10}$ through $R^{18}$ is fluorine and at least one is fluoroaliphatic with the further proviso that any pair of alpha-carbon fluoroaliphatic substituents, one member of the pair from one alpha carbon and one from another, can form a heterocyclic ring of from 4 to 7 members with the nitrogen atom ($N^o$).

10. The process for preparing tri-(fluoroaliphatic) alpha-fluosulfato amine comprising intimately contacting $SO_3$ under substantially anhydrous conditions, at a temperature in the range of 55° to 200°C under autogenous pressure, with tri-(fluoroaliphatic)amine of the formula:

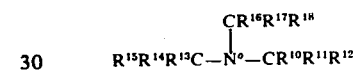

wherein $R^{10}$ through $R^{18}$ are alpha-carbon substituents selected from the class consisting of fluorine and fluoroaliphatic with the proviso that at least one of said $R^{10}$ through $R^{18}$ is fluorine and at least one is fluoroaliphatic with the further proviso that any pair of alpha-carbon fluoroaliphatic substituents, one member of the pair from one alpha carbon and one from another, can form a heterocyclic ring of from 4 to 7 members with the nitrogen atom ($N^o$).

11. The compound represented by the formula

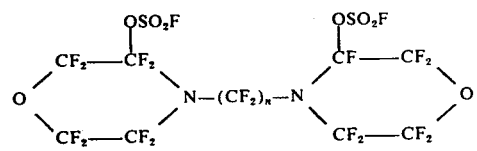

where $n$ is an integer less than 20.

* * * * *

UNITED STATES PATENT AND TRADEMARK OFFICE
CERTIFICATE OF CORRECTION

PATENT NO. : 3,956,293
DATED : May 11, 1976
INVENTOR(S) : Frank J. Pavlik

It is certified that error appears in the above-identified patent and that said Letters Patent are hereby corrected as shown below:

Column 5, lines 23-24,
"$(CR_3)_2NCR_2F\ SO_3 \longrightarrow (CR_3)_2NCR_2OSO_2F\ H_2O \longrightarrow (CR_3)_2NCR_2OH$" should read -- $(CR_3)_2NCR_2F \xrightarrow{SO_3} (CR_3)_2NCR_2OSO_2F \xrightarrow{H_2O} (CR_3)_2NCR_2OH$ --.

Column 7, lines 8-9, there should be a double bond inserted between "C" and "O".

Column 10, line 8, "hour" should read -- four --.

Column 14, first formula, "$+CF_2CF_2COOH)_2$" should read -- $+(CF_2CF_2COOH)_2$ --.

Column 14, second formula, delete the ")" after $CF_3COOH$.

Column 14, third formula, "$0(F_2COOH)_2$" should read -- $0(CF_2COOH)_2$ --.

Column 14, between the tenth and eleventh formulae, delete "o".

Column 15, line 15, "portic" should read -- protic --.

Column 16, lines 35-36, "in the skeletal chain" should be deleted from Claim 1.

Column 18, line 10, "$CR\ R^{11}R^{12}$" should read -- $CR^{10}R^{11}R^{12}$ --.

Signed and Sealed this

Fourth Day of January 1977

[SEAL]

Attest:

RUTH C. MASON
*Attesting Officer*

C. MARSHALL DANN
*Commissioner of Patents and Trademarks*